US012279748B2

(12) United States Patent
Lu et al.

(10) Patent No.: US 12,279,748 B2
(45) Date of Patent: *Apr. 22, 2025

(54) ENDOSCOPY SYSTEM WITH OFF-CENTER DIRECTION OF VIEW

(71) Applicant: SUZHOU ACUVU MEDICAL TECHNOLOGY CO. LTD., Suzhou Industrial Park (CN)

(72) Inventors: Fred Lu, Las Vegas, NV (US); Jian Zhang, San Mateo, CA (US); Allen Jiang, Fremont, CA (US)

(73) Assignee: SUZHOU ACUVU MEDICAL TECHNOLOGY CO. LTD, Suzhou Industrial Park (CN)

( * ) Notice: Subject to any disclaimer, the term of this patent is extended or adjusted under 35 U.S.C. 154(b) by 0 days.

This patent is subject to a terminal disclaimer.

(21) Appl. No.: 16/268,819

(22) Filed: Feb. 6, 2019

(65) Prior Publication Data

US 2019/0246884 A1     Aug. 15, 2019

Related U.S. Application Data

(60) Provisional application No. 62/630,718, filed on Feb. 14, 2018.

(51) Int. Cl.
*A61B 1/00*     (2006.01)
*A61B 1/005*    (2006.01)
(Continued)

(52) U.S. Cl.
CPC ...... *A61B 1/00042* (2022.02); *A61B 1/00009* (2013.01); *A61B 1/00045* (2013.01);
(Continued)

(58) Field of Classification Search
CPC ............ A61B 1/00179; A61B 1/00045; A61B 1/00066; A61B 1/00103; A61B 1/00144;
(Continued)

(56) References Cited

U.S. PATENT DOCUMENTS 3,856,000 A * 12/1974 Chikama ............ A61B 1/00183
600/176
3,896,793 A *  7/1975 Mitsui ................ A61B 1/00165
600/173
(Continued)

FOREIGN PATENT DOCUMENTS

CN     102028507     4/2011
CN     107638163     1/2018
(Continued)

OTHER PUBLICATIONS

PCT International Search Report No. PCT/IB2020/000470 dated Nov. 30, 2020.

*Primary Examiner* — Timothy J Neal
(74) *Attorney, Agent, or Firm* — Wissing Miller LLP

(57) ABSTRACT

An endoscopy system that includes a computer system with a high definition display monitor and a handheld portion. The handheld portion includes a re-usable handle portion and a single use portion that is configured to be disposed of following a single use. The single-use portion includes a substantially straight elongated cannula with an imaging module and illumination modules at its distal tip. The imaging module is mounted such that its direction of view (DOV) is at an oblique angle from the main longitudinal axis of the cannula.

17 Claims, 13 Drawing Sheets

(51) Int. Cl.
  *A61B 1/018*     (2006.01)
  *A61B 1/05*      (2006.01)
  *A61B 1/06*      (2006.01)
  *A61B 1/307*     (2006.01)
  *G02B 23/24*     (2006.01)

(52) U.S. Cl.
  CPC ...... *A61B 1/00066* (2013.01); *A61B 1/00103* (2013.01); *A61B 1/00144* (2013.01); *A61B 1/00179* (2013.01); *A61B 1/0057* (2013.01); *A61B 1/018* (2013.01); *A61B 1/05* (2013.01); *A61B 1/0676* (2013.01); *A61B 1/307* (2013.01); *G02B 23/2476* (2013.01); *G02B 23/2484* (2013.01); *A61B 1/00096* (2013.01); *G02B 23/2423* (2013.01)

(58) Field of Classification Search
  CPC ......... A61B 1/0057; A61B 1/018; A61B 1/04; A61B 1/00009; A61B 1/0676; A61B 1/307; A61B 1/05; A61B 1/00096; A61B 1/00078; A61B 1/0623; A61B 1/00142; A61B 1/00089; A61B 1/00101; A61B 1/00124; A61B 1/00039; A61B 1/00105; A61B 1/005; A61B 1/00071; A61B 1/00131; A61B 1/00183; A61B 1/051; A61B 1/00042; G02B 23/2476; G02B 23/2484; G02B 23/2423; G06Q 30/0185
  USPC .......................................... 600/136; 609/109
  See application file for complete search history.

(56) References Cited

U.S. PATENT DOCUMENTS

| | | | |
|---|---|---|---|
| 5,105,269 A * | 4/1992 | Nakamura | A61B 1/0646 |
| | | | 348/E5.038 |
| 5,792,045 A | 8/1998 | Adair | |
| 6,638,216 B1 * | 10/2003 | Durell | A61B 1/00183 |
| | | | 600/173 |
| 10,448,811 B2 | 10/2019 | London Brown et al. | |
| 11,589,740 B2 * | 2/2023 | Kim | A61B 1/00087 |
| 2005/0234294 A1 * | 10/2005 | Saadat | A61B 1/0008 |
| | | | 600/104 |
| 2006/0069306 A1 * | 3/2006 | Banik | A61B 1/0008 |
| | | | 600/118 |
| 2007/0118019 A1 * | 5/2007 | Mitani | A61B 1/00101 |
| | | | 600/176 |
| 2007/0232922 A1 * | 10/2007 | Kohno | A61B 8/4488 |
| | | | 600/459 |
| 2012/0123212 A1 * | 5/2012 | Dahmen | G02B 23/2423 |
| | | | 600/178 |
| 2012/0289858 A1 * | 11/2012 | Ouyang | A61B 1/045 |
| | | | 600/562 |
| 2013/0038836 A1 * | 2/2013 | Smith | A61B 3/0008 |
| | | | 351/211 |
| 2013/0046137 A1 * | 2/2013 | Zhao | A61B 1/05 |
| | | | 600/102 |
| 2014/0018622 A1 * | 1/2014 | Hoeg | A61B 1/00181 |
| | | | 600/173 |
| 2014/0275778 A1 * | 9/2014 | Gunday | A61B 1/00135 |
| | | | 600/109 |
| 2015/0230697 A1 * | 8/2015 | Phee | A61B 1/0057 |
| | | | 901/41 |
| 2015/0305603 A1 | 10/2015 | Gal | |
| 2016/0220324 A1 * | 8/2016 | Tesar | A61B 90/25 |
| 2017/0078583 A1 * | 3/2017 | Haggerty | H04N 23/55 |
| 2017/0095142 A1 * | 4/2017 | McDowall | A61B 1/00179 |
| 2017/0188795 A1 * | 7/2017 | Ouyang | A61B 1/00048 |
| 2017/0265879 A1 | 9/2017 | Washburn | |
| 2017/0325671 A1 * | 11/2017 | Hopkins, Jr. | A61B 1/045 |
| 2018/0256009 A1 * | 9/2018 | Ouyang | A61B 1/00052 |
| 2019/0142447 A1 * | 5/2019 | Cheng | A61B 17/2841 |
| | | | 606/142 |
| 2019/0246873 A1 * | 8/2019 | Lu | A61B 1/00039 |
| 2019/0261845 A1 | 8/2019 | Jensen | |
| 2020/0138271 A1 * | 5/2020 | Toth | A61B 1/0684 |
| 2020/0187751 A1 * | 6/2020 | Zheng | A61B 1/018 |
| 2021/0085169 A1 * | 3/2021 | Schmitt | A61B 1/05 |
| 2021/0298566 A1 * | 9/2021 | Levy | A61B 1/0625 |

FOREIGN PATENT DOCUMENTS

| | | | |
|---|---|---|---|
| CN | 2045622718 | 8/2018 | |
| CN | 109077698 | 12/2018 | |
| CN | 110868905 | 3/2020 | |
| KR | 101655653 | 9/2016 | |
| KR | 101655653 B1 * | 9/2016 | |
| WO | 2017192960 | 11/2017 | |
| WO | WO-2017192960 A1 * | 11/2017 | ........ A61B 17/295 |
| WO | 2019008103 | 1/2019 | |

* cited by examiner (A-A')

ENDOSCOPY SYSTEM WITH OFF-CENTER DIRECTION OF VIEW

REFERENCE TO RELATED APPLICATION

This patent application claims the benefit of and incorporates by reference U.S. Provisional Patent Application Ser. No. 62/630,718, filed on Feb. 14, 2018. All publications, patents, and patent applications mentioned in this specification are herein incorporated by reference to the same extent as if each individual publication, patent, or patent application was specifically and individually indicated to be incorporated by reference. Applicant's concurrently filed patent application Ser. No. 16/268,909, which has the same title and names the same inventors, also is hereby incorporated by reference.

FIELD

This patent specification generally relates to a medical device for use in tissue examinations and endoscopic surgery such as in hysteroscopy and urology. More particularly, some embodiments relate to endoscopy system that includes a disposable, single-use cannula and distal imaging module, and a reusable, multiple-use handle and display tower.

BACKGROUND

Direct vision medical procedures such as endoscopic procedures are used to examine certain parts of the body, including internal anatomies. For example, hysteroscopy examines the uterus, a cystoscopy examines the urinary bladder, a gastroscopy examines the esophagus, stomach, and/or small intestine, a bronchoscopy examines the throat, larynx, trachea, and/or lower airways, a sigmoidoscopy examines the rectum, a colonoscopy examines the rectum and/or colon, a colposcopy examines the cervix, vagina and/or vulva, a nasal endoscopy examines the nasal and sinus passages, and the like.

Traditionally endoscopic procedures are performed with expensive equipment. Such equipment may include cystoscopes, hysteroscopes, and various others. Such equipment may also include a display tower, which includes camera control unit and illumination control unit. Existing cystoscopes and hysteroscopes are usually reusable devices with metal cannulae and optical lens inside the metal shafts. Other types of cystoscopes and hysteroscopes may include flexible reusable devise, which a flexible cannula which articulation of the tip is often controlled by a pull wire and a joystick at proximal end. Following each procedure, the equipment may require sterilization which may be high in cost or difficult to operate, yet the sterilization or sanitization may not be effective. More recently, partly disposable endoscopes have become available—see for example U.S. Pat. Nos. 8,460,182 and 9,895,048.

An endoscope is an elongated tubular structure which is inserted into body cavities to examine them. A conventional endoscope includes a telescope with an objective lens at its distal end. The telescope includes an image-forwarding system. In rigid endoscopes it is a series of spaced-apart lenses. In flexible endoscopes it is a bundle of tiny optical fibers assembled coherently to forward the image. In digital endoscopes which are normally flexible scopes, the imaging sensor may reside at distal of the flexible cannula. However, when a physician maneuvers a deflectable tip with camera (a digital scope) of a cannula inside the patient, a view horizon may be lost and the physician may lose orientation.

It would therefore be desirable to overcome these challenges and provide a cystoscope and/or hysteroscope with disposable cannula portion at low cost. It would be desirable if such a device or system also capture images with a controllable horizontal view at reduced cost. At least some of these objectives will be satisfied by the devices described herein.

SUMMARY

According to some embodiments, an endoscopy system is described that includes: a computer processing system; a high-definition display having a display area of at least 12 inches diagonally in electrical communication with the computer processing system for receiving and displaying endoscopic images; and a handheld portion. The handheld portion includes: a multiple-use handle portion having mechanical and electrical couplers and a cable for electrical communication thereof with the computer processing system; and a single-use portion that includes a substantially straight elongated cannula having a central longitudinal cannula axis and a camera module mounted on a distal end, and mechanical and electrical couplers configured to mate with the mechanical and electrical couplers of the multiple-use handle portion to thereby releasably assemble the portions into an integral endoscope. The camera module has a selected oblique direction of view (DOV) with respect to the cannula axis. According to some embodiments, the camera module is mounted for motion relative to the cannula that selectively changes the DOV. The camera module can be mounted offset from the central cannula axis and the DOV is directed towards the central cannula axis. The single-use portion can be configured with a working channel to allow passage of surgical devices through the cannula and the distal tip. The distal tip can include a protrusion to accommodate the camera module being mounted with the oblique DOV without increasing the cross-section of the portion of the distal tip that is distal from the protrusion. The cannula can be mounted for rotation about the axis relative to a proximal portion of the single-use portion and further including a manual control on the multiple-use handle portion that is mechanically coupled with the cannula to rotate the cannula in response to manipulation of the control.

According to some embodiments, optical filtration can be provided at a distal end of the cannula causing the camera module to image selected wavelength range of light that is narrower than the range of white light. Control over the filtration can be configured to change the degree or nature of the filtration during use of the system in a medical procedure.

According to some embodiments a sterile package can be provided that houses the single-use portion before use in a medical procedure. According to some embodiments the single use portion can include a housing that has a distal portion from which the cannula extends distally and a proximal portion that mounts to the multiple-use handle through the couplers. The distal portion of the housing and the cannula can be mounted for rotation about the axis relative to the proximal portion of the housing.

According to some embodiments, and endoscope is described that includes: an image processor and an image display; a multiple-use handle remote from the image processor and the image display; an electrical cable connecting the multiple-use handle and the image processor; and a single-use portion releasably mating with the multiple-use portion through mechanical and electrical couplers on each to form an assembled instrument for a medical endoscopic procedure. The single-use portion can include a cannula mounted for rotation about a longitudinal axis thereof and an imaging module at the cannula's distal end selectively producing images and conveying the images through the electrical couplers and cable to the image processor for display on the display; a manual control mounted on the multiple-use handle and mechanically coupled to the cannula via the mechanical couplers to selectively rotate the cannula about the axis in response to manual manipulation of the control. The camera module can be mounted with a direction of view (DOV) angled relative to the axis. According to some embodiments, the single-use portion further includes a housing from which the cannula extends distally, the housing having a proximal portion that is releasably fixed to the multiple-use handle and a distal portion that is fixed relative to the cannula and rotates therewith relative to the proximal portion of the housing.

According to some embodiments, a method is described that includes: providing a multiple-use handle and a single-use portion that is in a sterile pouch and, when removed from the pouch, releasably mates with the multiple-use handle through mechanical and electrical couplers on each to form an assembled endoscope; inserting a cannula that is a part of the single-use portion in a patient's body cavity and taking images with a camera module at a distal end of the cannula, conveying the images through an electrical cable to a display that is remote from the multiple-use handle and displaying the images; and mechanically coupling a control knob on the multiple-use handle to the cannula through the mechanical couplers and selectively rotating the cannula about a longitudinal axis thereof relative to the multiple-use handle by manually operating the control knob while the cannula is in the body cavity. According to some embodiments, the DOV of the camera module can be selectively controlled relative to the axis to thereby angle the DOV at a selected angle relative to the axis.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION

Figure 1:
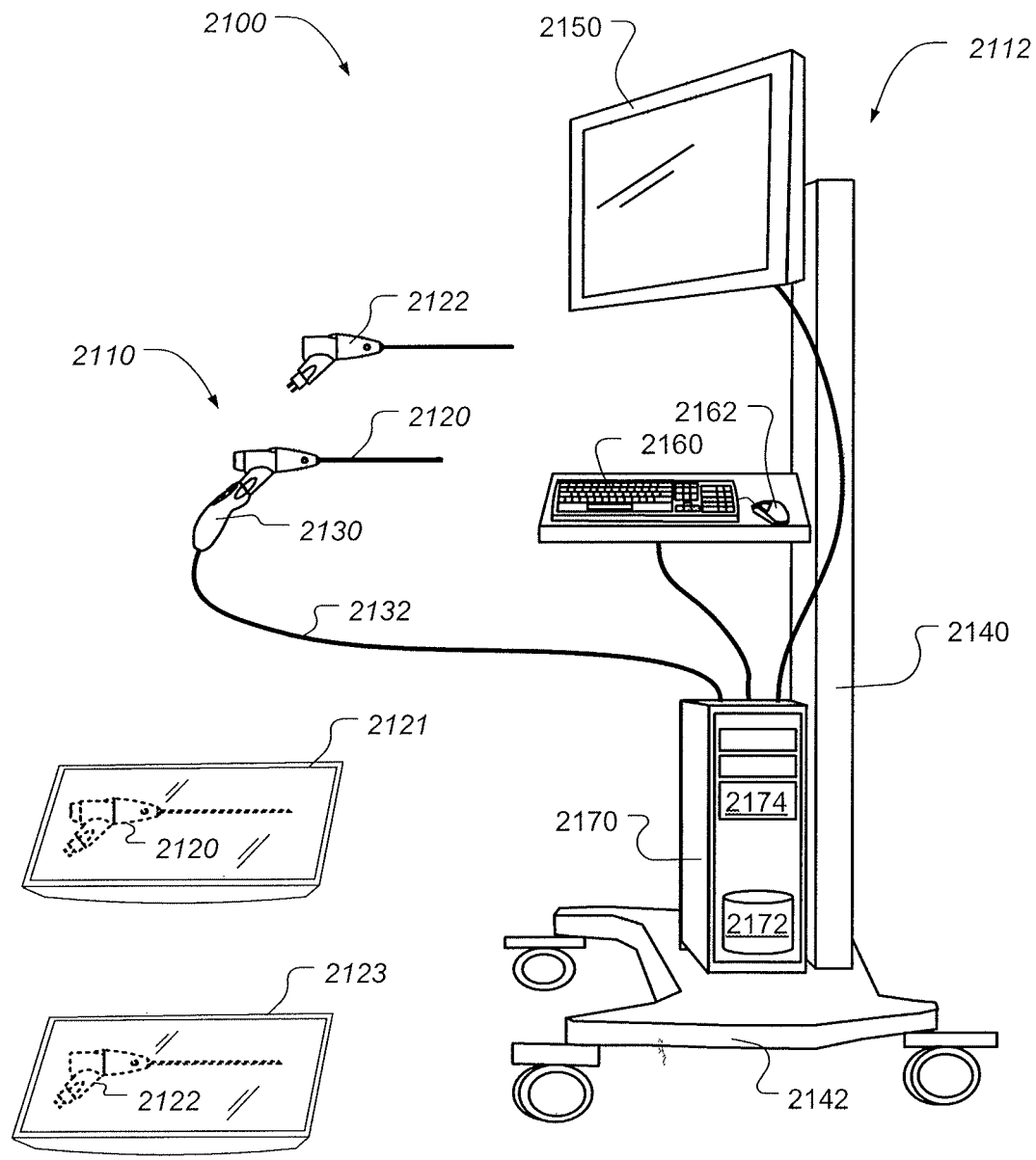
FIG. 1 shows an example of a endoscopy system, according to some embodiments.

A detailed description of examples of preferred embodiments is provided below. While several embodiments are described, it should be understood that the new subject matter described in this patent specification is not limited to any one embodiment or combination of embodiments described herein, but instead encompasses numerous alternatives, modifications, and equivalents. In addition, while numerous specific details are set forth in the following description in order to provide a thorough understanding, some embodiments can be practiced without some or all of these details. Moreover, for the purpose of clarity, certain technical material that is known in the related art has not been described in detail in order to avoid unnecessarily obscuring the new subject matter described herein. It should be clear that individual features of one or several of the specific embodiments described herein can be used in combination with features of other described embodiments or with other features. Further, like reference numbers and designations in the various drawings indicate like elements.

While some exemplary embodiments are directed at cystoscopes and/or hysteroscopes, one of skill in the art will appreciate that this is not intended to be limiting, and the devices described herein may be used for other therapeutic or diagnostic procedures and in other anatomical regions of a patient's body.

The embodiments disclosed herein can be combined in one or more of many ways to provide improved diagnosis and therapy to a patient. The disclosed embodiments can be, combined with prior methods and apparatus to provide improved treatment, such as combination with known methods of urological, or gynecological diagnosis, surgery and surgery of other tissues and organs, for example. It is to be understood that any one or more of the structures and steps as described herein can be combined with any one or more additional structures and steps of the methods and apparatus as described herein, the drawings and supporting text provide descriptions in accordance with embodiments.

Although the treatment planning and definition of treatment profiles and volumes as described herein are presented in the context of urological, or gynecological diagnosis or surgery, the methods and apparatus as described herein can be used to treat any tissue of the body and any organ and vessel of the body such as brain, heart, lungs, intestines, eyes, skin, kidney, liver, pancreas, stomach, uterus, ovaries, testicles, bladder, ear, nose, mouth, soft tissues such as bone marrow, adipose tissue, muscle, glandular and mucosal tissue, spinal and nerve tissue, cartilage, hard biological tissues such as teeth, bone and the like, as well as body lumens and passages such as the sinuses, ureter, colon, esophagus, lung passages, blood vessels and throat.

As used herein a processor encompasses one or more processors, for example a single processor, or a plurality of processors of a distributed processing system for example. A controller or processor as described herein generally comprises a tangible medium to store instructions to implement steps of a process, and the processor may comprise one or more of a central processing unit, programmable array logic, gate array-logic, or a field programmable gate array, for example.

As used herein, the terms distal and proximal refer to locations referenced from the apparatus, and can be opposite of anatomical references. For example a distal location of a probe may correspond to a proximal location of an elongate member of the patient, and a proximal location of the probe may correspond to a distal location of the elongate member of the patient.

According to various embodiments, a device includes a probing portion for direct insertion into a body cavity. The probing portion is brought into proximity to the tissue and/or area that is to be examined. As used herein, a probe encompasses an object inserted into a subject such as a patient.

FIG. 1 shows an example of an endoscopy system, according to some embodiments. The system 2100 includes a handheld portion 2110 and tower system 2112 which are interconnected via a cable 2132. The handheld portion 2110 includes a single-use disposable portion 2120 and handle portion 2130. The single-use portion 2120 is detachable from handle portion 2130 such that the handle portion 2130 is configured to be used many times. According to some embodiments, different types of versions of the single-use portions can be made available. In the example shown the single-use portion 2120 is configured for therapeutic use and includes a working channel (not shown) through which various devices such as surgical devices can pass through. In some embodiments, several different single-use portions may be supplied as a set of, for example, a single-use portion configured for therapeutic purposes and a single-use portion configured for diagnostic purposes, or a set of single-use portions that have different lengths and/or cannula diameters or arrangements of internal lumens. Also shown in FIG. 1 is a diagnostic single-use portion 2122 that is configured primarily for diagnostic, rather than therapeutic purposes, and does not have a working channel. As will be described in further detail, infra, both the therapeutic single-use portion 2120 and diagnostic single-use portion 2122 include a camera module and LED illumination modules on their distal tips as well as one or more internal lumens for carrying fluid. The tower system 2112 includes column 2140 mounted to a wheeled base 2142. The tower system 2112 also includes a display 2150, keyboard and mouse 2160 and 2162 and processing system 2170. According to some embodiments display monitor 2150 can be touch sensitive for receiving user input as well as high resolution. According to some embodiments display 2150 is configured to display high definition graphics at pixel resolutions of 1280×720, 1920×1080, 2048×1080, 2560×1440, 3840×2160, or higher. According to some embodiments, processing system 2170 can be a suitable personal computer or a workstation that includes one or more processing units 2174, input/output devices such as CD and/or DVD drives, internal storage 2142 such as RAM, PROM, EPROM, and magnetic type storage media such as one or more hard disks for storing the medical images and related databases and other information, as well as graphics processors suitable to power the graphics being displayed on display 2150. According to some embodiments, tower system 2112 is powered by a medical grade power supply (not shown). Also shown in FIG. 1 are sterile package or pouch 2121 containing a single-use portion 2120 configured for therapeutic purposes and sterile package or pouch 2123 the containing a single-use portion 2122 configured for diagnostic purposes.

Figure 2A:
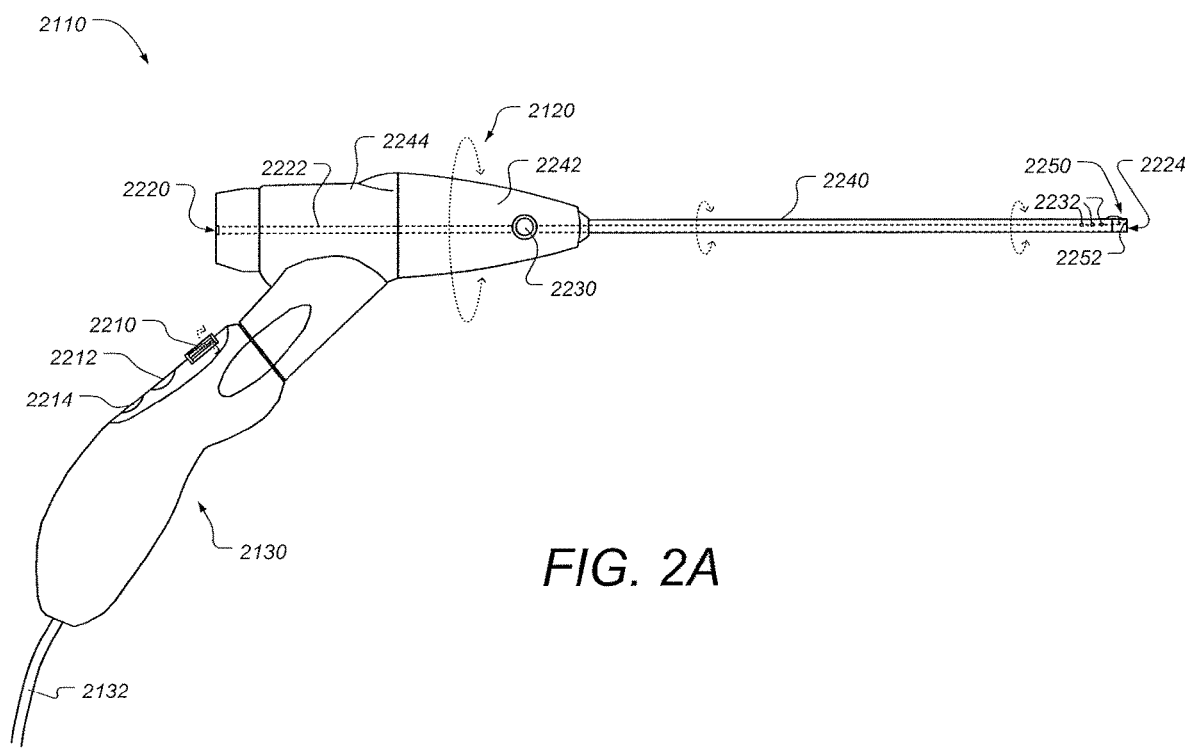
FIGS. 2A and 2B show side views of a hand-held portion of an endoscopy system, according to some embodiments.
Figure 2B:
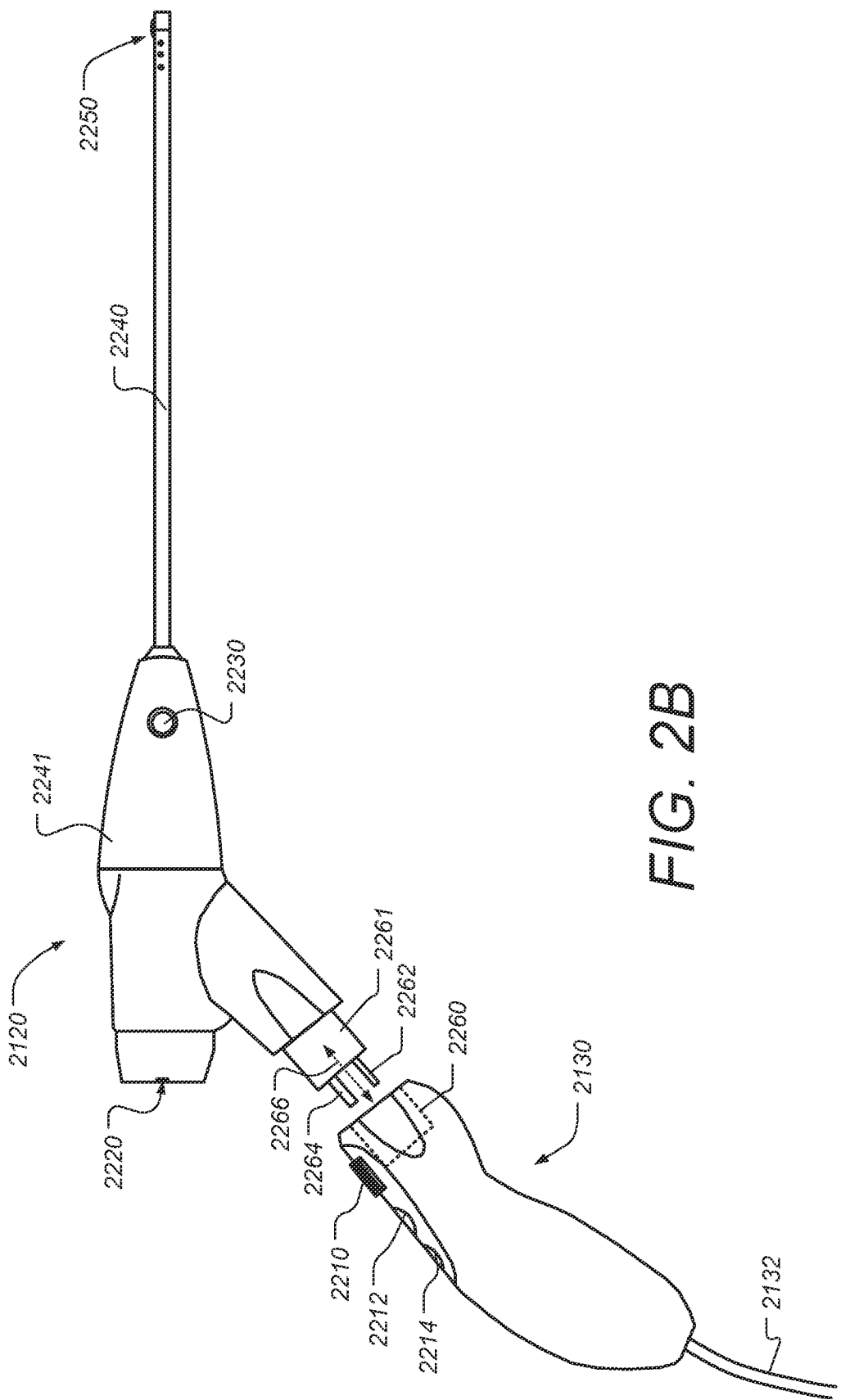

FIGS. 2A and 2B show side views of a hand-held portion of an endoscopy system, according to some embodiments. Hand-held portion 2110 generally includes a reusable handle portion 2130 and a single-use portion 2120. According to some embodiments, single-use portion 2120 may be delivered to the medical practitioner in pre-sterilized package and is intended to be disposed of after a single-use, while the handle portion 2130 is designed to be re-used many times. As mentioned, supra, the single-use portion 2120 in this example is a therapeutic single-use portion that includes a working channel. The therapeutic single-use portion 2120 includes an elongated cannula 2240 having a distal tip 2250. Distal tip 2250 includes a camera module 2252, working channel distal port 2224, and fluid ports 2232. Working channel 2222 is shown in dotted outline and extends from a proximal port 2220 through to the distal port 2224. According to some embodiments, the working channel has an inner diameter of about 3.2 mm such that many standard surgical devices can be disposed therein to carry out various surgical procedures. Examples of such devices include: injection needles, forceps, tubes, knives, snares, probes, coagulator devices, brushes, laser devices, microwave devices (e.g. for ablation), and photodynamic tools.

The cannula 2240 may be long, thin, and semi-rigid. According to some embodiments, the cross-section of cannula 2240 perpendicular to its main longitudinal axis may be substantially circular. It should be noted the cross-section may have any suitable shape such as oval shaped. The diameter of the cannula may differ depending on the sort of endoscopy, such as from 1 mm and up to 15 mm. Besides the working channel, cannula 2240 may have internal structures to support various functionalities. For example, the cannula may comprise one or more fluid channels in fluid communication with various fluid ports. The cannula may comprise one channel to be shared by an inflow and an outflow. Alternatively, the cannula may comprise two or more channels with separate inflow and outflow. According to some embodiments, cannula 2240 also includes a fluid lumen that is fluidically isolated from the working channel. The fluid lumen can be in fluid communication with the distal fluid ports 2232 as well as a proximal fluid port such as fluid port 2230. According to some embodiments another proximal fluid port is provided on the opposite side from port 2230. Cannula 2240 is also configured to accommodate a plurality of electrical conductors used to provide power, control signals to and receive video and image data from to the camera module and lighting modules at distal tip 2250. In some cases the conductors can be insulated and disposed within a separate lumen within cannula 2240, in other cases some or all of the conductors can be disposed within a lumen that is also used for another purpose (e.g. fluid and/or device/tool channel). According to some embodiments one or more optical fibers can pass through cannula 2240 for purposes of data transmission and/or supplying illumination light to distal tip 2250.

Handle portion 2130 is configured to be used many times and is adapted to repeatedly receive the single-use portions. Handle portion 2130 includes a main body that is dimensioned and shaped to allow secure and ergonomic grasping by the operator's hand. Handle portion 2130 also includes several buttons such as button 2212 and 2214 that can be configured to allow execution of common tasks during use. For example, the buttons 2212 and 2214 can be programmed to control LED lighting level (of LEDs, not shown, at the distal tip 2250), capture still images and/or start and stop recording to video images.

According to some embodiments, cannula 2240 is rotatable about its longitudinal axis relative to the handle portion 2130. In such cases handle 2130 can also include a cylindrical dial 2210 that is configured to rotate lumen 2240 (and distal tip 2250) as shown with the dotted arrows. According to some embodiments, the distal portion 2242 of a housing 2241 that surrounds a proximal portion of cannula 2240 rotates with the cannula 2240 while the proximal portion 2244 of the housing 2241 remains fixed relative to the handle portion 2130. FIG. 2B illustrates how the single-use portion 2120 can be mounted and removed from multiple-use handle portion 2130. In particular, handle portion 2130 includes a socket 2260 that is dimensioned to couple with male mating portion 2261 that protrudes from single-use portion 2120. The action of mounting and un-mounting is shown by dotted arrow 2266. Protruding from mating portion 2261 is an electrical connector 2262 and cannula 2264 that is used to provide rotation of cannula 2240 when dial 2210 is actuated. According to some embodiments cannula 2264 has a "D" shape cross section or other shape that provides secure rotational coupling between cannula 2264 and a female socket (not shown) in handle 2130.

According to some embodiments, the handle portion 2130 may house or comprise components configured to processing image data, generate control signals, provide power, or establish communication with other external devices. In some cases, the communication may be wireless or wired communication. For example, the wireless communications may include Wi-Fi, radio communications, Bluetooth, IR communications, or other types of direct communications. In some embodiments, the handle portion may be housing sensor assembly to measure a relative position between the cannula and the handle portion. In other embodiments, the sensor assembly may, measure relative position or orientation of the handle to its environment. In some cases, the handle portion may have a display device configured to provide a user input device or have any type user interactive component, such as a button, mouse, joystick, trackball, touchpad, pen, image capturing device, motion capture device, microphone, or touchscreen.

Figure 3:
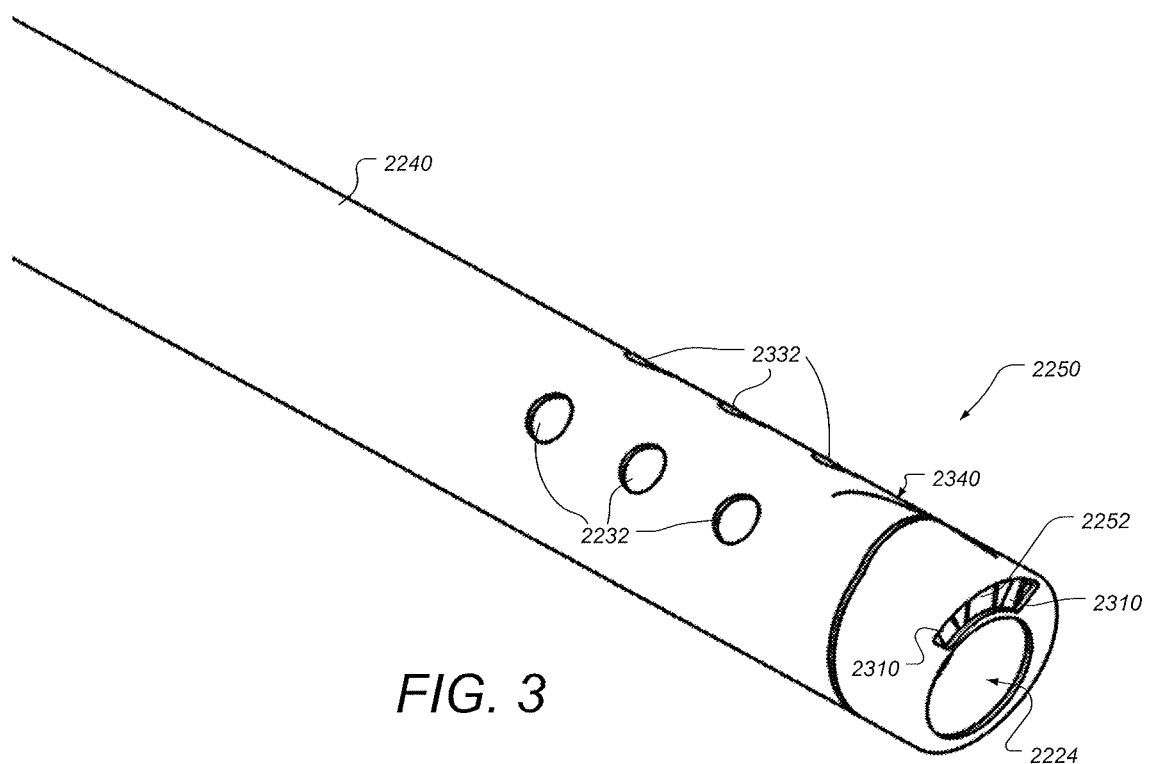
FIG. 3 is a perspective view showing further detail of the distal tip of a hand-held portion of an endoscopy system configured for therapeutic use, according to some embodiments.

FIG. 4 is a perspective view showing further detail of the distal tip of a hand- held portion of an endoscopy system configured for therapeutic use, according to some embodiments. Visible is the distal end of cannula 2240 and distal tip 2250. The distal tip 2250 includes camera module 2252 and LED light sources 2310. Also shown are the fluid p01is 2232 and 2332 and the distal working channel p01i 2224. According to some embodiments, the working channel p01i 2224 is also configured for in-flow (flowing fluid out of the device and into the patient) and fluid p01is 2232 and 2332 are configured for out-flow (into the device and out of the patient). Also visible in FIG. 3 is a slight protrusion or bump 2340 that rises slightly higher than the rest of the cannula 2240 on the distal tip 2250. The bump 2340 is provided to as to allow a tilted mounting of the camera module 2252 while still maintaining an over-all low diameter to the cannula 2240 and distal tip 2250.

Figure 4A:
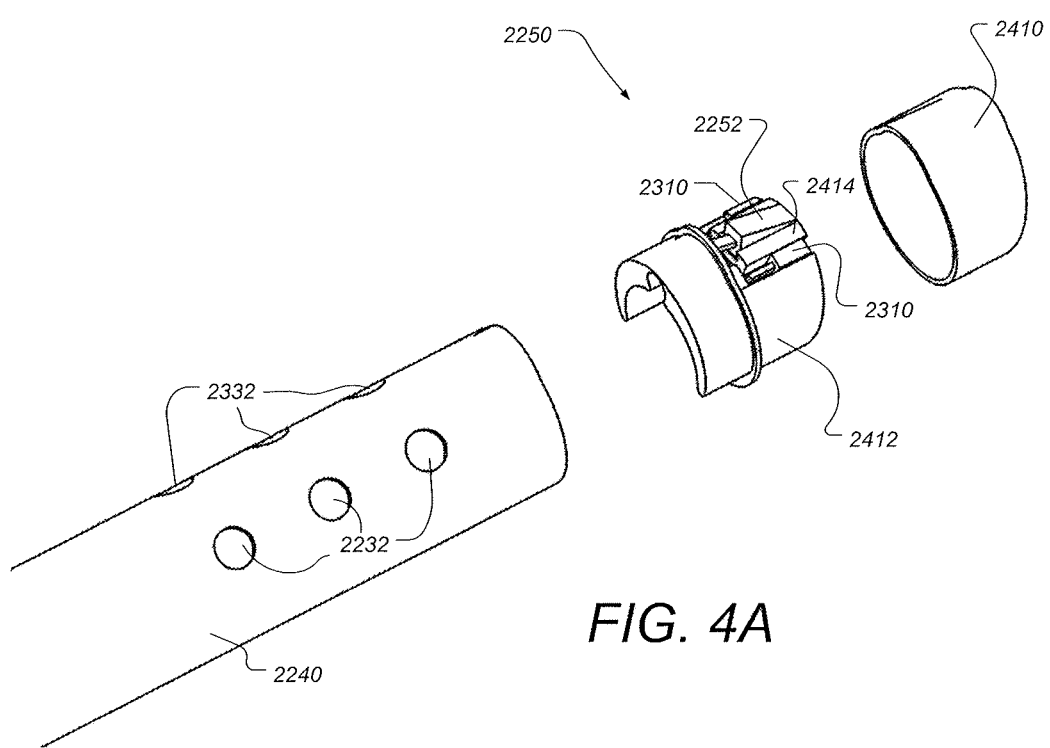
FIG. 4A is a perspective view showing further detail of the distal tip of a hand-held portion of an endoscopy system configured for therapeutic use, according to some embodiments.

FIG. 4A is a perspective view showing further detail of the distal tip of a hand-held portion of an endoscopy system configured for therapeutic use, according to some embodiments. Visible in this exploded view is how the distal tip 2250 is attached to the cannula 2240. Distal tip 2250 includes a tip housing 2410 that surrounds the distal portion tip module 2412. The proximal portion of module 2412 is inserted and into and bonded to the distal end of cannula 2240. Module 2412 includes can include a separate carrier 2414 onto which camera module 2252 and LEDs 2310 are mounted. According to some embodiments, carrier 2414 is not separate but rather is integrated into module 2412. Note that module 2412 is configured in this example to hold camera module in a slightly downward angle of view. That is, the camera module 2252 is pointed downwards such that its view is biased towards the working channel distal port 2224 shown in FIG. 3 and FIG. 4C.

Figure 4B:
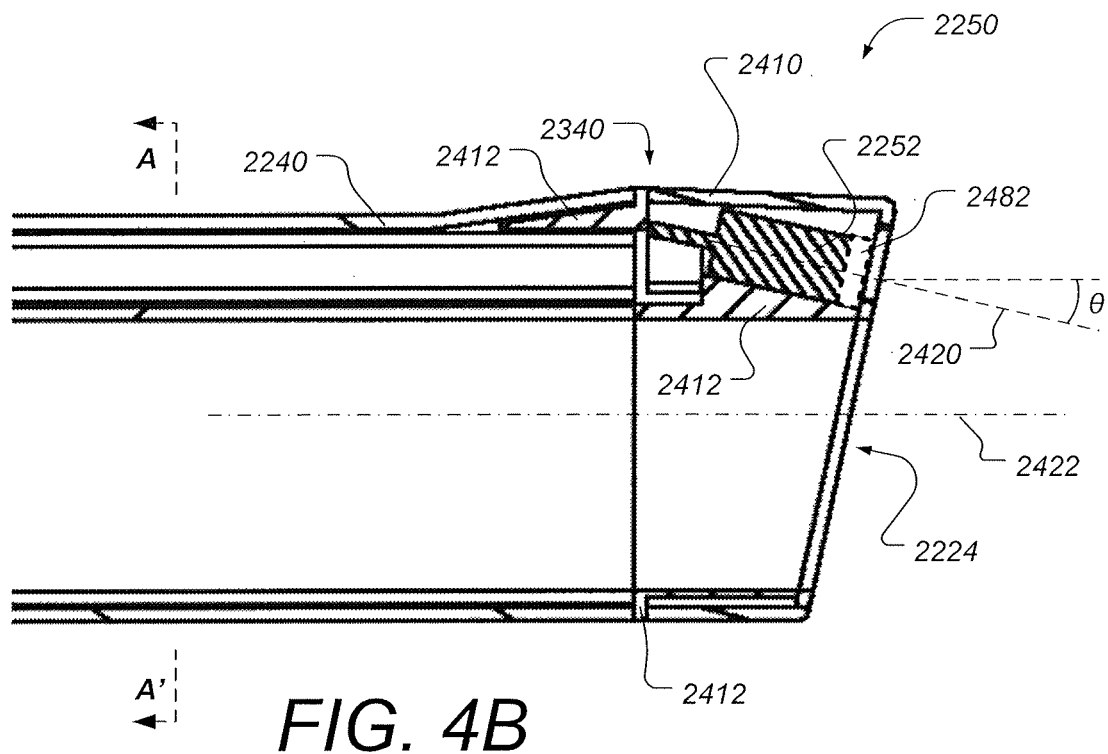
FIG. 4B is a cross section showing further detail of the distal tip of a hand-held portion of an endoscopy system configured for therapeutic use, according to some embodiments.

According to some embodiments, the tip housing 2410 can made from a suitable material such as acrylic. In some cases, at least a portion of the housing 2410 is transparent such that the lines-of-sight of the camera module 2252 is not be obstructed by the housing 2410 while the optical axis of the camera module 2252 is not aligned with the axis of the cannula 2240 (as shown in FIG. 4B). In some cases, one or more sides of the housing 2410 is be transparent. In some cases, a portion of a side of the housing 2410 is transparent. In some embodiments, at least 10%, 20%, 30%, 40%, 50%, 60%, 70%, 80%, 90%, or 100% of a total surface of the housing 2410 is transparent. In some cases, other structures that may be in the direction of the lines-of-sight may also be made of transparent material. The housing 2410 may be completely transparent so that images captured using optical components within the housing are not distorted or affected by the housing. In some cases, the housing 2410 may include anti-glare or anti-reflective coatings. The housing 2410 may or may not comprise a material that may filter out undesired wavelengths of light. The housing 2410 may or may not function as a secondary lens. The housing 2410 may or may not affect a field of view of the imaging device. According to some embodiments, a sufficient portion of the housing 2410 may be transparent to allow for panoramic images to captured using the imaging device. The optical components may be capable of rotating at least 360 degrees without obstruction, such as by rotating the cannula 2240 about its main axis. In some cases, at least a portion of the housing 2410 may be opaque or selectively let light pass through such that illumination light from the distal illumination means (e.g. LEDs) may be filtered in order to achieve better imaging effect.

According to some embodiments, camera module 2252 comprises optical elements and image sensor for capturing image data. The image sensor may be configured to generate image data in response to wavelengths of light. A variety of image sensors may be employed for capturing image data such as complementary metal oxide semiconductor (CMOS) or charge-coupled device (CCD). In some cases, the image sensor may be provided on a circuit board. The circuit board may be an imaging printed circuit board (PCB). The circuit board may comprise a plurality of electronic elements for processing the image signal. For instance, the circuit for a CCD sensor may comprise A/D converters and amplifiers to amplify and convert the analog signal provided by the CCD sensor. Optionally, the image sensor may be integrated with amplifiers and converters to convert analog signal to digital signal such that a circuit board may not be required. In some cases, the output of the image sensor or the circuit board may be image data (digital signals) can be further processed by a camera circuit or processors of the camera. In some cases, the image sensor may comprise an array of optical sensors.

The imaging sensor of camera module 2252 may capture an image frame or a sequence of image frames at a specific image resolution. The image frame resolution may be defined by the number of pixels in a frame. The image resolution may be greater than or similar to about 352×420 pixels, 480×320 pixels, 720×480 pixels, 1280×720 pixels, 1440×1080 pixels, 1920×1080 pixels, 2048×1080 pixels, 3840×2160 pixels, 4096×2160 pixels, 7680×4320 pixels, or 15360×8640 pixels. The imaging sensor of camera module 2252 may have pixel size no more than 1 micron, 2 microns, 3 microns, 5 microns, 10 microns, 20 microns and the like. The camera module may be, for example, a 4K camera or a camera with a higher resolution. Pixels of camera may be square. Alternatively, pixels may be non-square. The imaging device may capture color images, greyscale images, or non-white light images and the like.

According to some embodiments, one or more lenses together with other optical components may be used for different purposes to achieve various optical effects. Other optical components may include any type of optical elements. For instance, an example of an optical element may include an optical filter 2482 (shown in FIG. 4B) that may be used to selectively transmit or reject a wavelength or range of wavelengths. Examples of filters may include a bandpass interference filter that may transmit a portion of an electromagnetic spectrum, while rejecting all other wavelengths. One or more notch filters may be provided as an example of an optical filter 2482. A notch filter may reject a portion of the spectrum, while transmitting all other wavelengths. Edge or dichroic filters may transmit wavelengths that are either greater than the cut-on or shorter than the cut-off wavelengths. Another example of a filter 2482 may include a color substrate filter, which may utilize the filter material's inherent adsorption and transmission properties. A neutral density (ND) filter may evenly reduce transmission across a portion of the spectrum. In some cases, UV/infrared cut filters may be used for blocking infrared light and some UV light while allowing a full spectrum camera to take normal pictures. Examples of optical elements may include filters, mirrors, prisms, lenses, dichroic filters, beam splitters, optical fibers, or any other types of optical elements. Optical elements may pass light therethrough, reflect light, disperse light, refract light, focus light, filter light, or perform any other actions on the light. Any optical elements or combinations of optical elements may be provided. According to some embodiments filtration from optical filter 2482 is electronically controllable. In such cases the filtration control can be provided by use of a button on handle portion 2130 (e.g. buttons 2212 or 2214 shown in FIGS. 2A and 2B).

The optical assembly of camera module 2252 may further comprise components that are useful for adjusting the light path. In some embodiments, the optical assembly may include zoom lens for which the focal length or angle of view can be varied.

One or more light sources may be positioned at the distal tip 2250. The light source(s) may be a light-emitting diode (LED), an organic LED (OLED), a quantum dot, or any other suitable light source. In some cases, the light source may be Dual Tone Flash LED Lighting. The light source may be any other suitable optical illumination delivered by optical fiber from light sources inside the disposable cannula, the handle, or any other part of the device.

Figure 4C:
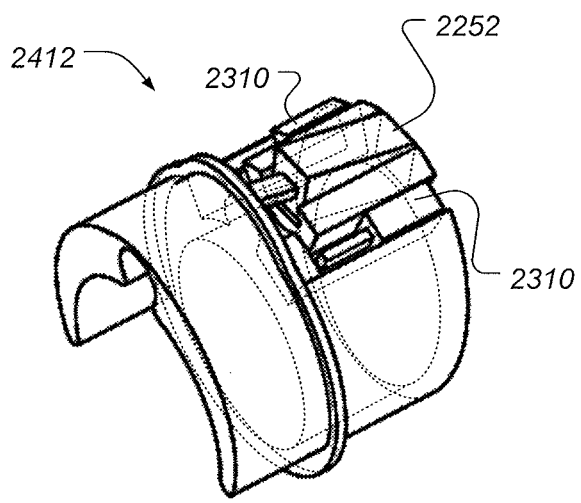
FIG. 4C is a perspective view showing further details of a distal portion tip module for an endoscopy system configured for therapeutic use, according to some embodiments.

FIG. 4B is a cross section view showing further detail of the distal tip of a hand-held portion of an endoscopy system configured for therapeutic use, according to some embodiments. A shaft on a conventional endoscope may have an optical prism inside rod lenses at certain degrees near the distal end to be suitable for many applications. For example, the optical prism may provide a direction of view (DOV) at various degrees (e.g., 30 degrees, 70 degrees or any number between 0 and 180 degrees) in order to enlarge a field of view. However, when an imaging sensor is situated at the distal tip, such optical prism may cause a very large packaging at distal end or greatly increase the cost of the camera module. According to some embodiments, a device with multiple DOVs is provided by positioning the imaging device at various angles such that the optical axis of the imaging device intersects with the longitude axis of the cannula at the imaging device. For instance, as shown in FIG. 4B, the camera module 2252 can be positioned such that the optical axis (i.e., DOV) 2420 of the camera module 2252 is oblique to the axis 2422 of the cannula 2240 by and DOV angle θ. According to some embodiments, the DOV angle θ is equal to 0 degrees, 5 degrees, 10 degrees, 12.5 degrees, 15 degrees, 20 degrees, 25 degrees, 30 degrees, 35 degrees, 40 degrees, 45 degrees, 50 degrees, 55 degrees, 50 degrees, 55 degrees, 60 degrees, 65 degrees, 70 degrees, 75 degrees, 90 degrees, 120 degrees, 150 degrees, up to 180 degrees or any number in between. FIG. 4C is a perspective view showing further details of distal portion tip module 2412.

The camera module 2252 has a suitable size and dimension that is suitable for being enclosed in the distal tip 2250. In some instances, the camera module may have a maximum dimension (e.g., length, width, height, diameter, diagonal) of less than or equal to about: 0.5 mm, 1 mm, 2 mm, 3 mm, 4 mm, 5 mm, 5.5 mm, or any number up to 100 mm. According to some embodiments the camera module 2252 has a diameter or "height" of about 1.6 mm. The camera module may have a footprint (which may refer to the lateral cross-sectional area encompassed by the imaging device) of less than or equal to about: 50 cm$^2$, 10 cm$^2$, 5 cm$^2$, 2 cm$^2$, 1 cm$^2$, 0.01 cm$^2$ or less. In some instances, the camera module may weigh no more than 0.5 kg, 0.1 kg, 0.05 kg, 0.01 kg, 5 g, 1 g or less. The camera module may occupy a total volume of space of about equal to or less than 250 cm$^3$, 200 cm$^3$, 175 cm$^3$, 150 cm$^3$, 125 cm$^3$, 100 cm$^3$, 75 cm$^3$, 50 cm$^3$, 40 cm$^3$, 30 cm$^3$, 20 cm$^3$, 15 cm$^3$, 10 cm$^3$, 5 cm$^3$, 1 cm$^3$, 0.1 cm$^3$ 0.05 cm$^3$ or less.

According to some embodiments, the DOV angle θ shown in FIG. 4B may be manually controlled. The angle θ can be fixed during the operation of the device 2100. Alternatively or additionally, the angle θ can be varied during the operation, for example as illustrated in FIG. 10B. In some case, the imaging device may be affixed to an attachment means of the distal tip at a desired angle prior to insertion. Alternatively, the imaging device may be rotatably coupled to the distal end such that the angle can be adjusted during operation of the device. The imaging device can be affixed or coupled to the distal tip via any suitable attachment means such as using adhesives (e.g., glue), fasteners (e.g., bolts), complementary mechanical features or a combination of the above.

Figure 4D:
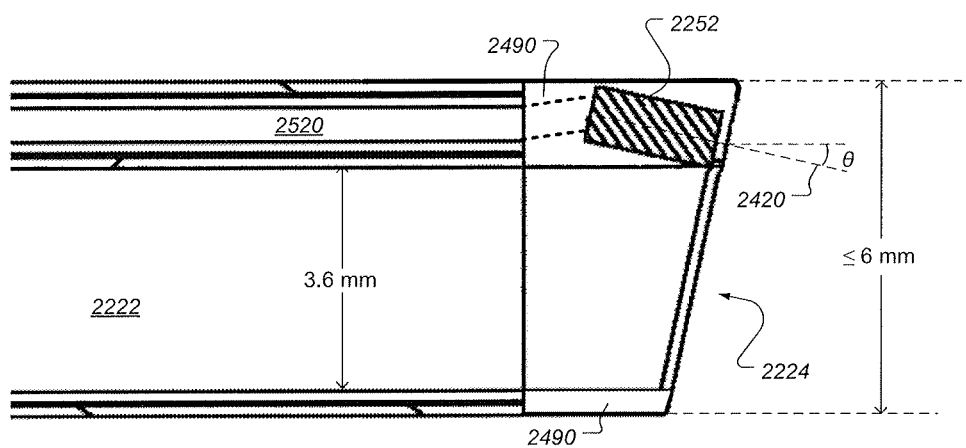
FIG. 4D is a cross section view showing further detail of the distal tip of a hand-held portion of an endoscopy system configured for therapeutic use, according to some other embodiments.

FIG. 4D is a cross section view showing further detail of the distal tip of a hand-held portion of an endoscopy system configured for therapeutic use, according to some other embodiments. In this case, distal tip cover 2410 and module 2412, are replaced with a single molded tip module 2490. Using a single piece saves space due to less walls being used. Using a single molded tip module 2490 allows a DOV angle θ of about 12 degrees, working channel 2222 of 3.6 mm, camera module height of 2.4 mm and overall all diameter of about 6 mm without any bump or protrusion (such as bump 2340 shown in FIG. 4B).

Figure 5:
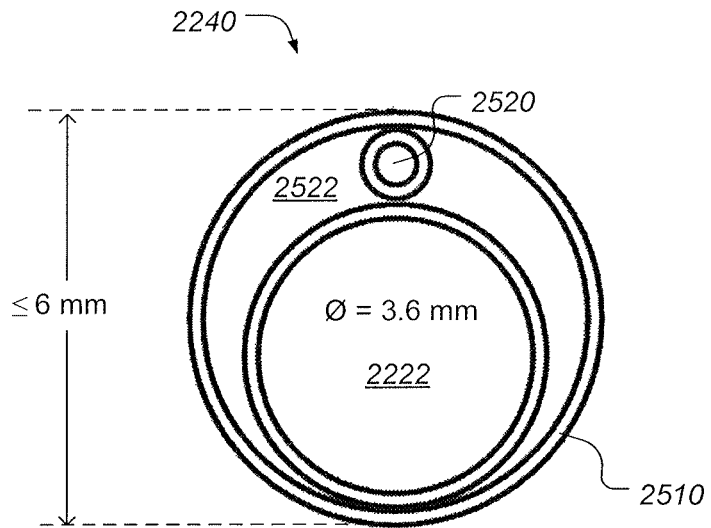
FIG. 5 is a cross section of cannula used in an endoscopy system configured for therapeutic use, according to some embodiments.

FIG. 5 is a cross section of cannula used in an endoscopy system configured for therapeutic use, according to some embodiments. FIG. 5 shows a cross section of the cannula 2240 along A-A' shown in FIG. 4B. Within the outer wall 2510 of cannula 2240 there are three fluidically separate lumens: working channel 2222, secondary fluid lumen 2522 and cable lumen 2520. The working channel 2222 is used, as described, to allow passage of a surgical device. According to some embodiments, the working channel 2222 is also used to carry fluid. Fluid lumen 2522 is also used to carry fluid. According to some embodiments, working channel 2222 is configured for in-flow (flowing fluid out of the device and into the patient) via distal working channel port 2224 shown in FIGS. 2A, 3 and 6, and fluid lumen 2522 is used for out-flow (flow fluid into the device and out of the patient) via fluid ports 2232 and 2332 shown in FIG. 3. Cable lumen 2530 is configured to accommodate a plurality of electrical conductors used to provide power, control signals to and receive video and image data from to the camera module and lighting modules at distal tip 2250. According to some embodiments one or more optical fibers can pass through lumen 2522 for purposes of data transmission and/or supplying illumination light to distal tip 2250.

Figure 6:
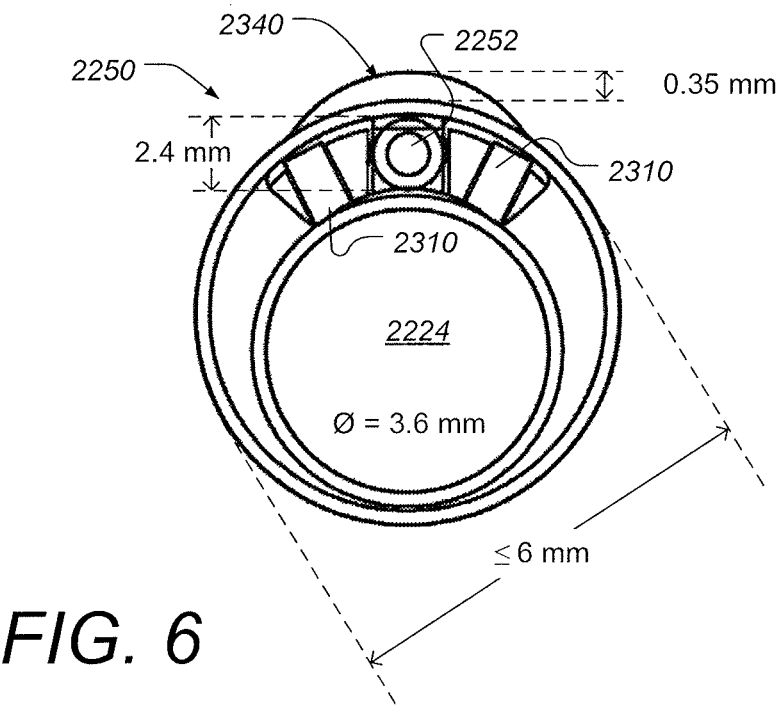
FIG. 6 is frontal view of a distal tip of an endoscopy system configured for therapeutic use, according to some embodiments.

FIG. 6 is frontal view of a distal tip of an endoscopy system configured for therapeutic use, according to some embodiments. Shown in this view are working channel port 2224, camera module 2252 and LEDs 2310. Also shown is the bump 2340. According to some embodiments the bump 2340 extend a maximum of about 0.35 mm above the upper surface of lumen 2240 and tip 2250 when the camera module 2252 is 2.4 mm high and the DOV angle θ is about 12 degrees. According to some embodiments, in cases where the camera module is about 1.6 mm the distal tip can be made without a bump 2340. According to some embodiments, the bump 2340 is between 0.1 mm and 0.5 mm high in cases where the camera module is greater than about 2.0 mm high and the DOV angle θ is greater than about 10 degrees.

Figure 7A:
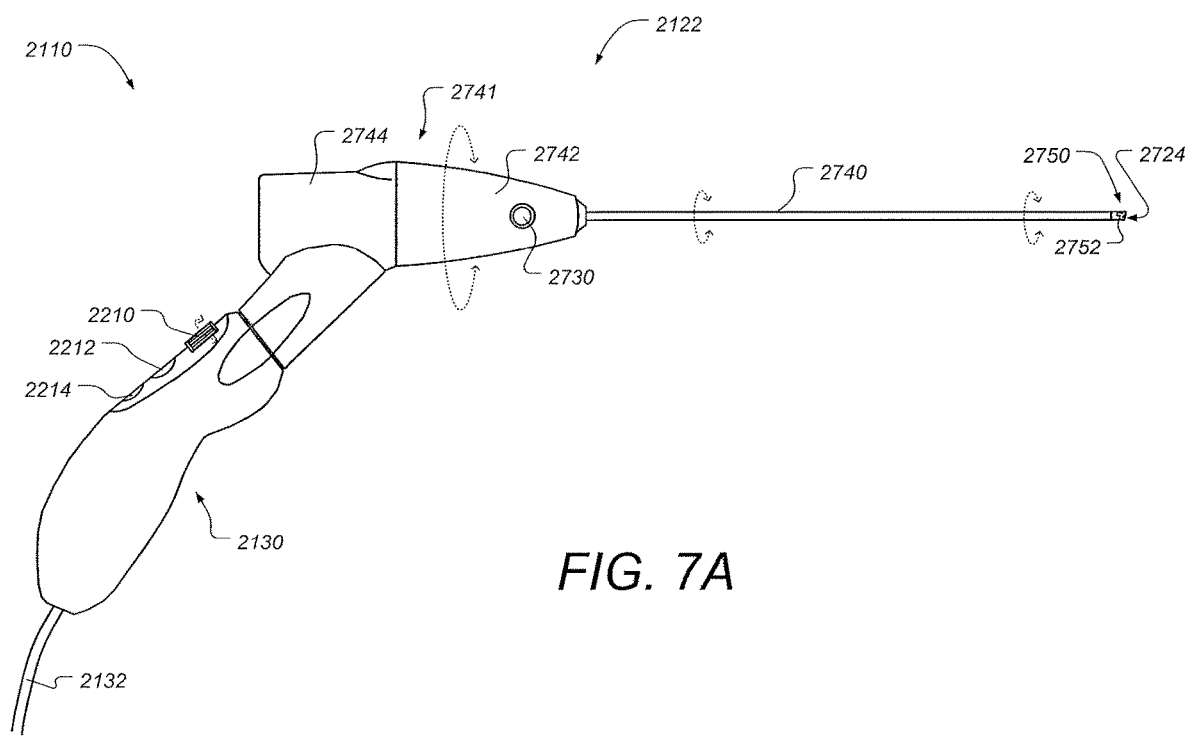
FIGS. 7A and 7B show side views of a hand-held portion of an endoscopy system configured for diagnostic use, according to some embodiments.
Figure 7B:
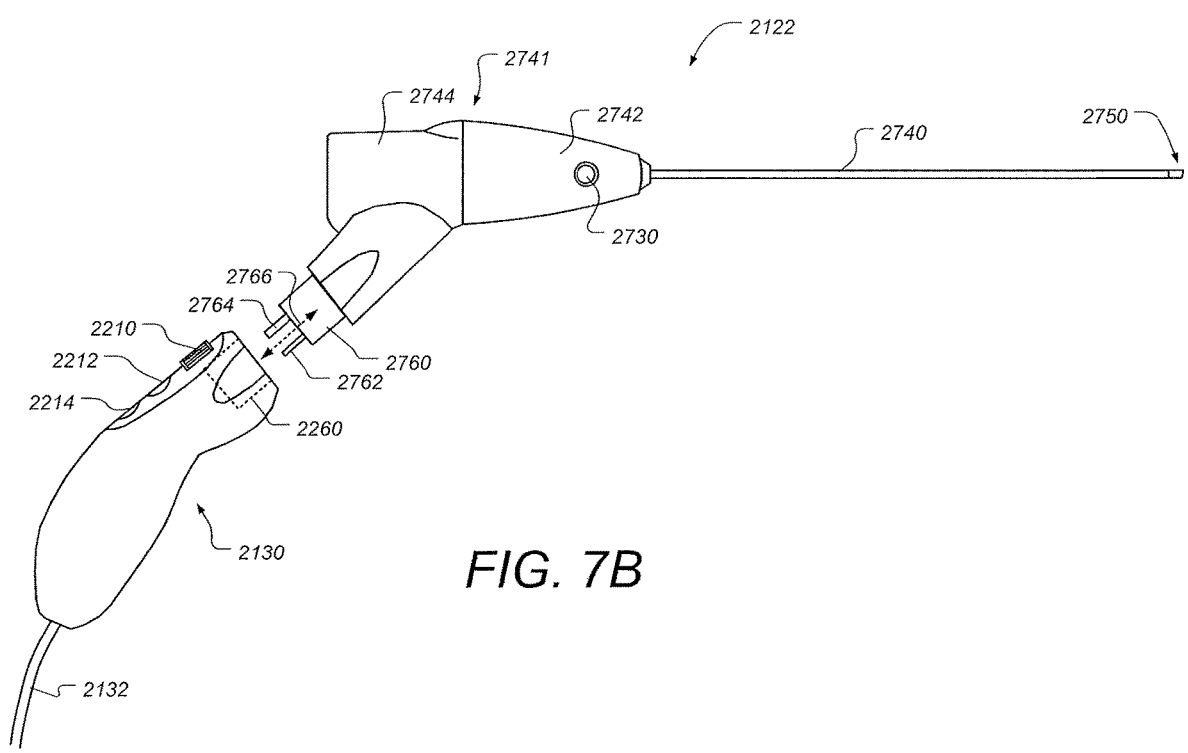

FIGS. 7A and 7B show side views of a hand-held portion of an endoscopy system configured for diagnostic use, according to some embodiments. Hand-held portion 2110 in this case includes a reusable handle portion 2130 and a diagnostic single-use portion 2122. Note that many of the components of single-use portion 2122 are similar or identical to the components of single-use portion 2120 shown in and described with respect to FIGS. 2A, 2B, 3, 4, 5 and 6. Many of the embodiments that are shown in those figures and described herein for single-use portion 2120 apply equally to single-use portion 2122 and will not be repeated for purposes of clarity. According to some embodiments, single-use portion 2122 may be delivered to the medical practitioner in pre-sterilized package and is intended to be disposed of after a single-use, while the handle portion 2130 is designed to be re-used many times. As mentioned, supra, the single-use portion 2122 in this example is a diagnostic single-use portion that does not include a working channel.

The diagnostic single-use portion 2122 includes an elongated cannula 2740 having a distal tip 2750. Distal tip 2750 includes a camera module 2752, and distal fluid ports 2724.

The cannula 2740 may be long, thin, and semi-rigid. According to some embodiments, the cross-section of cannula 2740 perpendicular to its main longitudinal axis may be substantially circular. It should be noted the cross-section may have any suitable shape such as oval shaped. The diameter of the cannula may differ depending on the sort of endoscopy, such as from 1 mm and up to 15 mm. Cannula 2740 may have internal structures to support various functionalities. For example, the cannula may comprise one or more fluid channels in fluid communication with various fluid ports. The cannula may comprise one channel to be shared by an inflow and an outflow. Alternatively, the cannula may comprise two or more channels with separate inflow and outflow. The fluid lumen can be in fluid communication with the distal fluid ports 2724 as well as a proximal fluid port such as fluid port 2730. Cannula 2740 is also configured to accommodate a plurality of electrical conductors used to provide power, control signals to and receive video and image data from to the camera module and lighting modules at distal tip 2750. In some cases the conductors can be insulated and disposed within a separate lumen within cannula 2740, in other cases some or all of the conductors can be disposed within a lumen that is also used for another purpose (e.g. fluid and/or device/tool channel). According to some embodiments one or more optical fibers can pass through cannula 2740 for purposes of data transmission and/or supplying illumination light to distal tip 2750.

According to some embodiments, cannula 2740 is rotatable about its longitudinal axis relative to the handle portion 2130. In such cases handle 2130 can also include a cylindrical dial 2210 that is configured to rotate lumen 2740 (and distal tip 2750) as shown with the dotted arrows. According to some embodiments, the distal portion 2742 of the housing 2741 rotates with the cannula 2740 while the proximal portion 2744 of the housing 2741 remains fixed relative to the handle portion 2130. FIG. 7B illustrates how the single-use portion 2122 can be mounted and removed from multiple-use handle portion 2130. In particular, handle portion 2130 includes a socket 2260 that is dimensioned to couple with male mating portion 2760 that protrudes from single-use portion 2120. The action of mounting and un-mounting is shown by dotted arrow 2766. Protruding from mating portion 2760 is an electrical connector 2762 and shaft 2764 that is used to provide rotation of cannula 2740 when dial 2210 is actuated.

Figure 8:
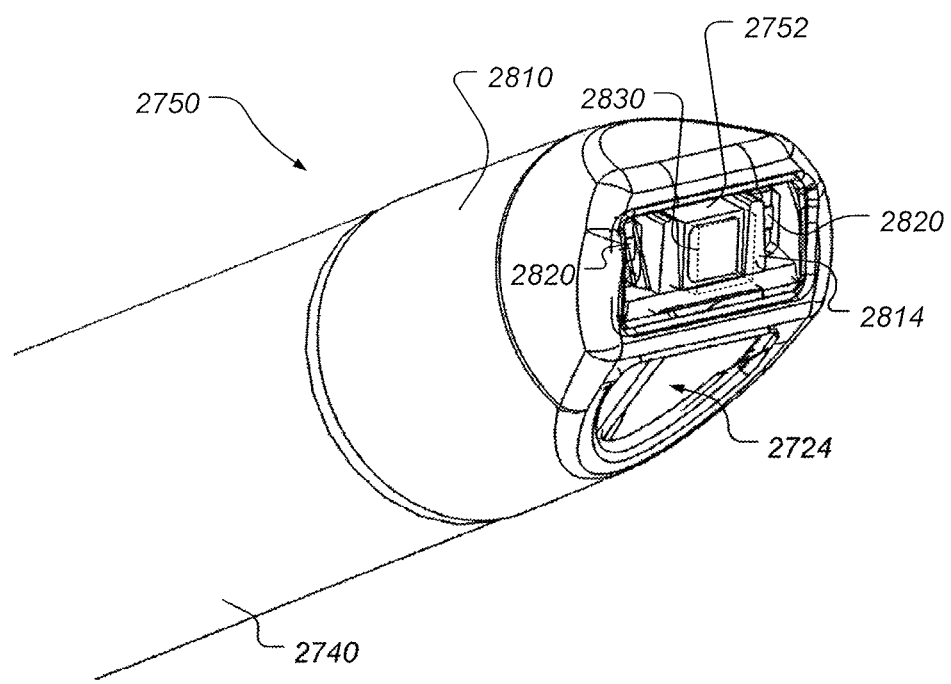
FIG. 8 is a perspective view showing further detail of the distal tip of a hand-held portion of an endoscopy system configured for diagnostic use, according to some embodiments.

FIG. 8 is a perspective view showing further detail of the distal tip of a hand-held portion of an endoscopy system configured for diagnostic use, according to some embodiments. Visible is the distal end of cannula 2740 and distal tip 2750. The distal tip 2750 includes camera module 2752 and LED light sources 2820. Also shown are two fluid ports 2724. According to some embodiments, one fluid port is configured for in-flow (flowing fluid out of the device and into the patient) and is configured for out-flow (into the device and out of the patient). Similarly to distal tip 2250 (e.g. shown in FIG. 4) distal tip 2750 is a separate assembly attached to the cannula 2740. Distal tip 2750 includes a tip housing 2810 that surrounds a distal portion tip module (not shown). The proximal portion of the distal tip module is bonded to the distal end of cannula 2740. A carrier 2814 holds camera module 2752 and LEDs 2820. Note that carrier 2814 is configured in this example to hold camera module in a slightly downward DOV angle. That is, the camera module 2752 has a DOV pointed downwards such that its view is biased towards the fluid ports 2724.

Figure 9:
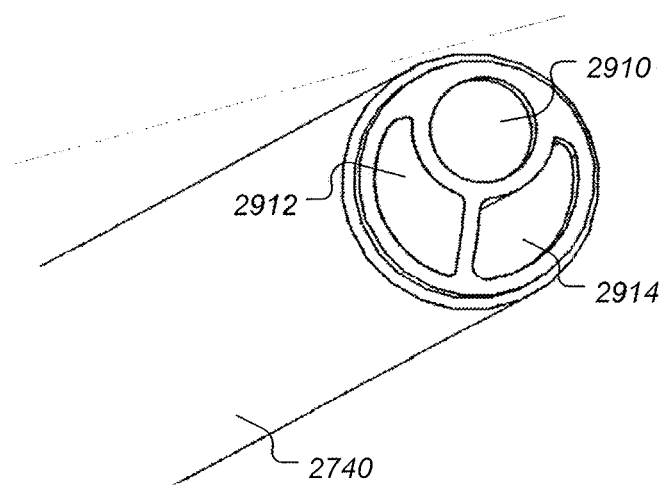
FIG. 9 is a perspective view showing some of the inner structures of a cannula configured diagnostic endoscopic use, according to some embodiments.

FIG. 9 is a perspective view showing some of the inner structures of a cannula configured diagnostic endoscopic use, according to some embodiments. In this view, three lumens are visible. Lumen 2910 that is used for carrying the electrical wires that connect the camera module and LEDs with the electrical connector 2762. Lumens 2912 and 2914 are configured for carrying fluid between the proximal fluid ports (e.g. 2730 in FIGS. 7A and 7B) and the distal fluid ports 2724.

Figure 10A:
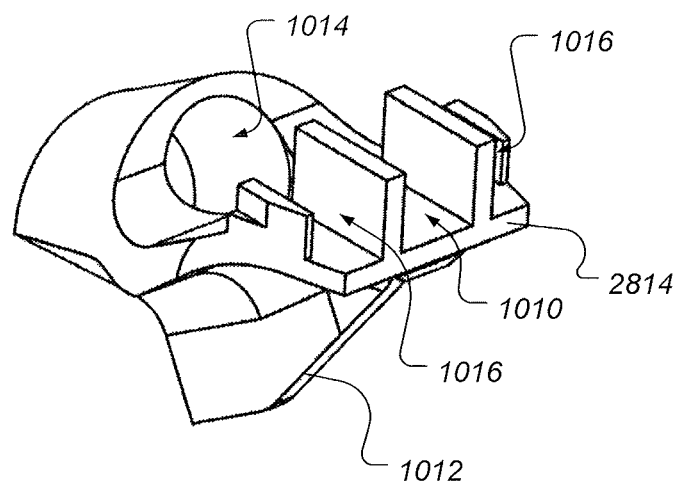
FIGS. 10A and 10B are perspective and side views of distal tip carrier module used with an endoscopy system configured for diagnostic use, according to some embodiments.
Figure 10B:
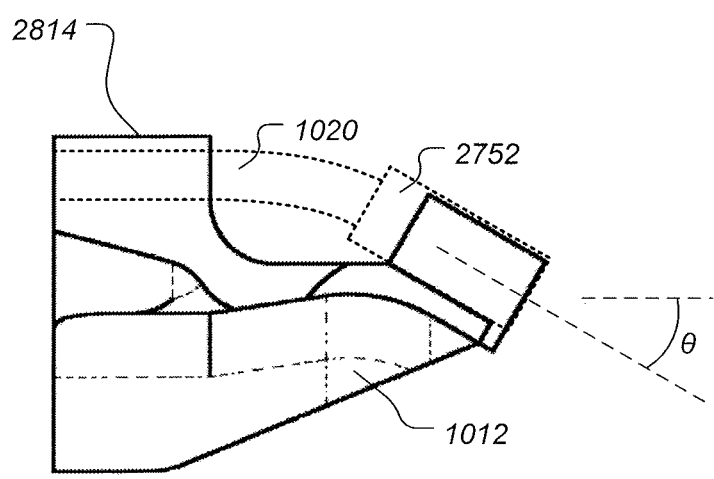

FIGS. 10A and 10B are perspective and side views of distal tip carrier module used with an endoscopy system configured for diagnostic use, according to some embodiments. FIG. 10A shows that carrier 2814 has a central slot 1010 for holding the camera module 2752 at a downward tilting angle. On either side of slot 1010 are slots 1016 that hold LED units 2820, also at a downward tilting angle. There is circular passage 1014 formed in carrier 2814 for accommodating the cable or wires used to carrying power, controls signals, data and/or image signals between the handle portion 2130 (shown, e.g. in FIGS. 1 and 7A) and the camera module and LEDs. Also shown in FIG. 10A is the lower wall 1012 that separates the two fluid lumens 2912 and 2914 in cannula 2740 (shown in FIG. 9). FIG. 10B shows in dotted outline the camera module 2752 and cable 1020 being held by carrier 2814. FIG. 10B also shows the DOV angle θ.

Figure 11A:
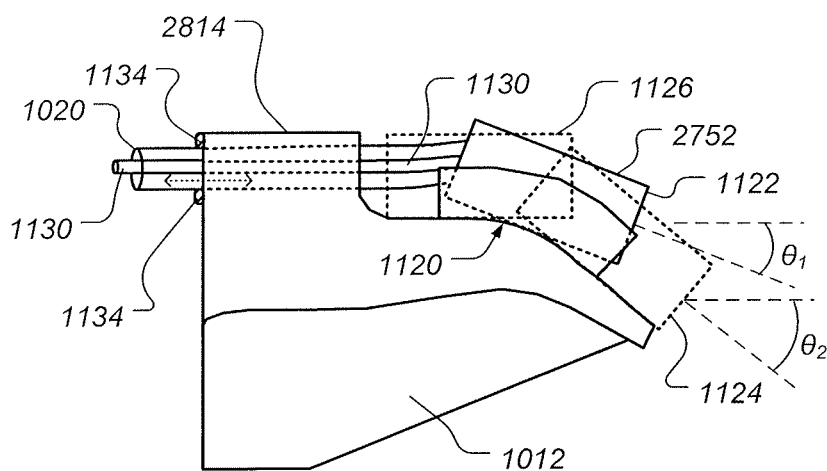
FIGS. 11A and 11B illustrate aspects of a variable direction of view endoscopy system, according to some embodiments.
Figure 11B:
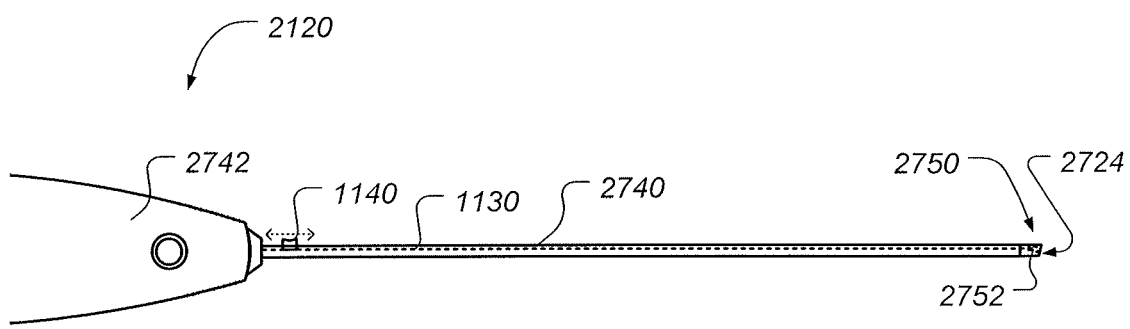

In embodiments allowing for varying the angle θ, the camera module 2252 or 2752 can be mounted for sliding motion along a curved raceway. FIGS. 11A and 11B illustrate aspects of a variable direction of view endoscopy system, according to some embodiments. In FIG. 11A, raceway 1120 is curved, such that when the camera module 2752 is pushed in the distal direction along the raceway 1120 the angle θ increases and when the camera module 2752 pulled in the proximal direction along the raceway 1120 the angle θ decreases. In FIG. 11A, $\theta_2 > \theta_1$. Cable 1020 can be used to push and pull the camera module 2252 or 2752 for this purpose if sufficiently stiff. Alternatively, cable 1020 can be stiffened with a suitable insert or outer coating, or a separate stiff wire 1130 can be used to push or pull the camera module 2752 and thus change the angle θ. The cable 1020, or the separate stiff wire, can extend from the camera module 2252 or 2752 to a manually operated button or joystick on some or all of the single-use portions 2120 and 2122 or 2740. FIG. 11B shows a tab 1140 mounted near the proximal end of cannula 2740. Tab 1140 is fixed to stiff wire 1130. Manual manipulation of tab 1140 selects or changes the angle θ. This selection can be done at the time of manufacturing the single-use portion, before commencing a medical procedure with the single-use portion, or during the medical procedure. An alternative structure for selecting and changing the angle θ can use a cam mount for the camera module and control wires coupling the camera module to a button or joystick at a proximal portion of the single-use portion and configured such that manual manipulation of the button or joystick moves the camera module along the cam to change the angle θ as needed or desired. Yet another alternative structure comprises a pivoting mount for the camera module 2750 that allows the camera module to pivot about an axis transverse to the longitudinal axis of the cannula, in response to manipulation of like cable or wires, to thereby change the angle θ as needed or desired. Note that in the case of FIGS. 11A and 11B, a thin layer of flexible and stretchable material 1134 can be added to prevent liquid leaks into the wire lumen of the cannula. The material 1134 can be soft rubber or other suitable material. The soft material 1134 is glued to the edge of cannula tip structure 2814 and surrounding the camera module edges. When the camera module 2752 moves, the thin flexible and stretchable can prevent liquid leaks into the cannula wire lumen.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. An endoscopy system comprising:
   a computer processing system;
   a high-definition display having a display area of at least 12 inches diagonally in electrical communication with the computer processing system for receiving and displaying endoscopic images; and
   a handheld portion comprising:
   a handle portion having a cable for electrical communication thereof with the computer processing system; and
   a cannula portion that extends along a central longitudinal axis, has an outer diameter, and comprises (a) a straight elongated cannula, (b) a carrier that extends distally from the cannula, is affixed thereto, and has a curved raceway portion, (c) an imaging module that is mounted for motion along and against said curved raceway and is coupled with said computer processing system through said handle portion, and (d) a cap covering the imaging module; and
   wherein said imaging module has a direction of view (DOV) optical axis with respect to said central longitudinal axis and is configured to concurrently move distally relative to said carrier and radially toward said longitudinal axis along said curved raceway thereof to thereby change said DOV optical axis to directions intersecting the longitudinal axis at a location distal from the cannula and the cap while maintaining the outer diameter of said cannula portion and wherein said imaging module in the entirety thereof remains within the cannula portion and the cap.

2. An endoscopy system according to claim 1, wherein said imaging module is mounted such that said DOV optical axis is directed towards the central longitudinal axis in at least some positions of the imaging module relative to said curved raceway and is directed along said central longitudinal axis in at least one of said positions.

3. An endoscopy system according to claim 1, wherein said cannula portion is configured with a working channel to allow passage of surgical devices.

4. An endoscopy system according to claim 1, wherein said cannula is mounted for rotation about said central longitudinal axis relative to a proximal portion of the cannula portion and further including a manual control that is mechanically coupled with the cannula to rotate the cannula relative to said proximal portion of the cannula portion in response to manipulation of said manual control.

5. An endoscopy system according to claim 1, further including an optical filtration at a distal end of said cannula portion causing said imaging module to image a selected wavelength range of light that is narrower than the range of white light.

6. An endoscopy system according to claim 5, further including a control over said optical filtration configured to change the degree or nature of said optical filtration during use of said system in a medical procedure.

7. An endoscopy system according to claim 1, further including a sterile package housing said cannula portion before use thereof in a medical procedure.

8. An endoscopy system according to claim 1, in which said cannula portion comprises a housing that has a distal portion from which said cannula extends distally and a proximal portion and wherein said distal portion of the housing and said cannula are mounted for rotation about said central longitudinal axis relative to said proximal portion of the housing.

9. An endoscope comprising:
an image processor and an image display;
a handle portion remote from the image processor and the image display;
an electrical cable connecting the handle portion and the image processor;
a cannula portion secured to said handle to form an assembled instrument for a medical endoscopic procedure;
said cannula portion comprising (a) a cannula mounted for rotation about a longitudinal axis thereof relative to said handle portion, (b) an imaging module mounted at a distal end of the cannula portion for selectively producing images and conveying said images to the image processor for display on said display, (c) a curved raceway at a distal portion of the cannula portion, wherein said imaging module is configured to concurrently move distally along said curved raceway and radially toward the longitudinal axis without changing a cross-section of said distal end of the cannula portion;
a manual control mounted on said handle portion and mechanically coupled to said cannula to selectively rotate the cannula about said central longitudinal axis relative to the handle portion in response to manual manipulation of the manual control; and wherein said imaging module is mounted with a direction of view (DOV) optical axis and wherein said moving of the imaging module along said curved raceway changes the DOV optical axis relative to the longitudinal axis to intersect the longitudinal axis at a location distal from the cannula while the imaging module in its entirety remains in the cannula portion.

10. The endoscope of claim 9, in which said cannula portion further comprises a housing from which said cannula extends distally, said housing having a proximal portion and a distal portion that is fixed relative to the cannula and rotates therewith relative to the proximal portion of the housing.

11. The endoscope of claim 9, in which said imaging module is mounted for said movement to selectively change the DOV optical axis while the cannula is in a body cavity during a medical procedure using said cannula.

12. The endoscope of claim 9, including a sterile pouch in which said cannula portion is enclosed.

13. The endoscope of claim 9, further comprising an optical filtering that selectively passes to said imaging module only desirable light wavelengths.

14. The endoscope of claim 13, in which said optical filtering selectively changes a range of the wavelengths passed to the imaging module.

15. A method comprising:
providing a handle portion and a cannula portion that form an endoscope;
inserting a cannula that is a part of the cannula portion in a patient's body cavity, taking images with an imaging module that is at a distal portion of the cannula portion, and conveying said images through an electrical cable to a display that is remote from the handle and displaying the images; and
mechanically coupling one or more control knobs on the handle portion to said cannula and selectively and concurrently both rotating the cannula about a longitudinal axis thereof relative to said handle portion and changing a direction of a DOV optical axis of said imaging module relative to said distal portion of the cannula portion by moving the imaging module concurrently both in a distal direction and in a radial direction along a curved path such that the imaging module in its entirety moves simultaneously in directions both along and across said longitudinal axis along said curved path to positions in which the optical axis intersects the longitudinal axis at a location distal from the cannula, without increasing the cross-section of said distal portion of the cannula portion, by manually operating said one or more control knobs while the cannula is in said body cavity.

16. The method of claim 15, further including selectively controlling a direction of view (DOV) optical axis of the imaging module relative to the longitudinal axis by said moving the imaging module through said curved path to thereby angle the DOV optical axis at a selected angle relative to said longitudinal axis.

17. The method of claim 15, further including in said cannula portion a housing that has a distal portion from which said cannula extends distally and a proximal portion, and said rotating of the cannula comprises rotating said distal portion of the housing with the cannula relative to said proximal portion of the housing.

* * * * *